United States Patent
Pullagurla et al.

(10) Patent No.: US 10,556,924 B2
(45) Date of Patent: Feb. 11, 2020

(54) PROCESS FOR THE PREPARATION OF PASIREOTIDE

(71) Applicant: BIOPHORE INDIA PHARMACEUTICALS PVT. LTD., Hyderabad (IN)

(72) Inventors: Manik Reddy Pullagurla, Hyderabad (IN); Radha Nagarapu, Hyderabad (IN); Jagadeesh Babu Rangisetty, Hyderabad (IN)

(73) Assignee: BIOPHORE INDIA PHARMACEUTICALS PVT. LTD., Hyderabad (IN)

( * ) Notice: Subject to any disclaimer, the term of this patent is extended or adjusted under 35 U.S.C. 154(b) by 0 days.

(21) Appl. No.: 15/738,876

(22) PCT Filed: Jun. 22, 2016

(86) PCT No.: PCT/IN2016/050195
§ 371 (c)(1),
(2) Date: Dec. 21, 2017

(87) PCT Pub. No.: WO2016/207912
PCT Pub. Date: Dec. 29, 2016

(65) Prior Publication Data
US 2018/0186829 A1 Jul. 5, 2018

(30) Foreign Application Priority Data
Jun. 22, 2015 (IN) .............. 3119/CHE/2015

(51) Int. Cl.
*C07K 1/10* (2006.01)
*C07K 7/64* (2006.01)
*C07K 1/06* (2006.01)

(52) U.S. Cl.
CPC ............... *C07K 1/10* (2013.01); *C07K 1/063* (2013.01); *C07K 7/64* (2013.01)

(58) Field of Classification Search
None
See application file for complete search history.

(56) References Cited

U.S. PATENT DOCUMENTS

| | | | |
|---|---|---|---|
| 7,473,761 B2 | 1/2009 | Albert et al. | |
| 2011/0166320 A1 | 7/2011 | Albert et al. | |

FOREIGN PATENT DOCUMENTS

| | | |
|---|---|---|
| CN | 103467575 A | 12/2013 |
| CN | 103641894 A | 3/2014 |
| CN | 104447962 A | 3/2015 |

OTHER PUBLICATIONS

Isidro-Llobet et al. ('Amino acid-protecting groups' Chem Rev v109 2009 pp. 2455-2504). (Year: 2009).*

Translation of CN103641894, retrieved from http://translationportal.epo.org/emtp/translate/?ACTION=description-retrieval&COUNTRY=CN&ENGINE=google&FORMAT=docdb&KIND=A&LOCALE=en_EP&NUMBER=103641894&OPS=ops.epo.org/3.2&SRCLANG=zh&TRGLANG=en on Mar. 11, 2019, 29 pages (Year: 2019).*

International Patent Application No. PCT/IN2016/050195; Written Opinion and the Search Report; dated Nov. 16, 2016; 8 pages.

* cited by examiner

*Primary Examiner* — Karlheinz R. Skowronek
*Assistant Examiner* — Ronald T Niebauer
(74) *Attorney, Agent, or Firm* — BakerHostetler

(57) ABSTRACT

The present invention relates to a novel process for the preparation of Pasireotide of formula 11 [Cyclo [Phe-{4-(OCO—NH—CH$_2$—CH$_2$—NH$_2$)) Pro}-Phg-DTrp-Lys-Tyr (Bzl)]]. The invention also relates to a novel intermediate compound of formula 8 and process thereof which is used for preparation of compound of formula 11.

2 Claims, No Drawings

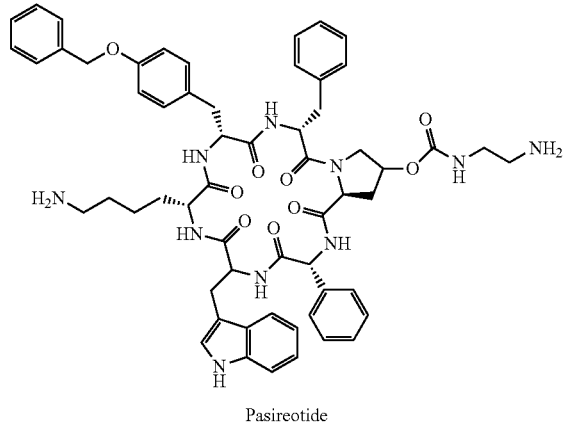

(Compound 11)

Pasireotide

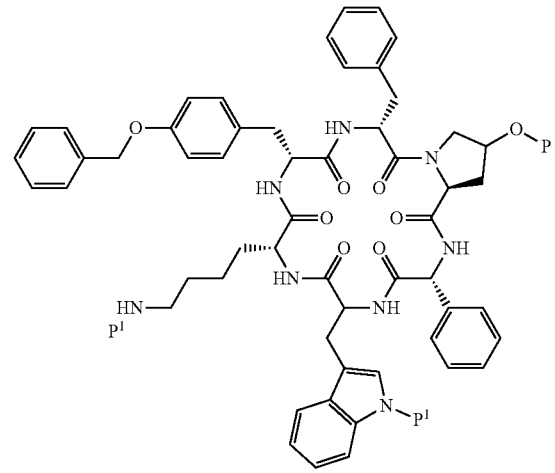

Compound 8

PROCESS FOR THE PREPARATION OF PASIREOTIDE

CROSS-REFERENCE

This application is a national stage application of PCT/IN2016/050195, with an international filing date of Jun. 22, 2016, and claims the benefit of Indian Patent Application No. 3119/CHE/2015, filed Jun. 22, 2015, the entire contents of both are incorporated herein by reference.

FIELD OF THE INVENTION

The present invention relates to a novel process for the preparation of Pasireotide, Cyclo[Phe-{4-(OCO—NH—CH$_2$—CH$_2$—NH$_2$)Pro}-Phg-DTrp-Lys-Tyr(Bzl)] of formula (11). The present invention also relates to a novel intermediate compound of formula (8) and process thereof which is used for preparation of compound of formula 11.

BACKGROUND OF THE INVENTION

Pasireotide is a synthetic long-acting cyclic hexapeptide with somatostatin-like activity. It is chemically known as (2-Aminoethyl) carbamic acid (2R,5S,8S,11S,14R,17S,19aS)-11-(4-aminobutyl)-5-benzyl-8-(4-benzyloxybenzyl)-14-(1H-indol-3ylmethyl)-4,7,10,13,16,19-hexaoxo-17-phenyloctadecahydro-3a,6,9,12,15,18-hexaazacyclopentacyclooctadecen-2-yl-ester. It is marketed as a diaspartate salt called Signifor®, which is used in the treatment of Cushing's disease.

The cyclic peptide sequence of Pasireotide is represented as Cyclo[Phe-{4-(OCO—NH—CH$_2$—CH$_2$—NH$_2$)) Pro}-Phg-DTrp-Lys-Tyr(Bzl)].

U.S. Pat. No. 7,473,761 discloses Pasireotide along with other somatostatin analogues. Not many synthetic proce-

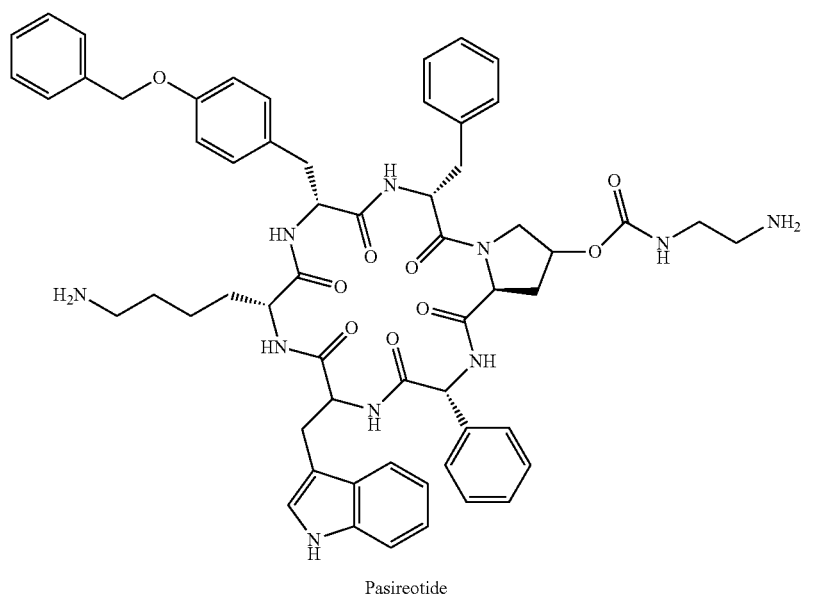

(11)

Pasireotide

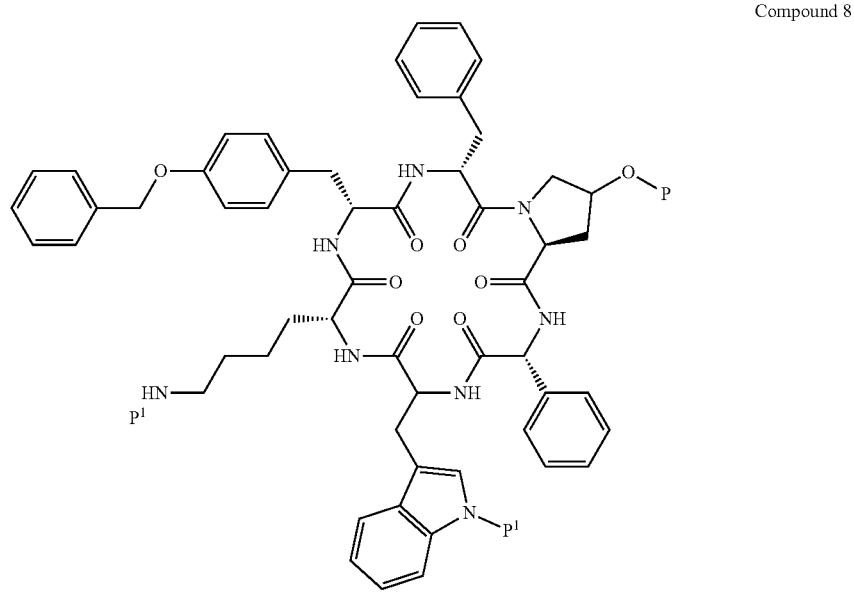

Compound 8 dures for Pasireotide are known in the art. US publication 20110166320 discloses a method for the preparation of Pasireotide by solid phase synthesis. The process involves, sequential addition of amino acids (Fmoc/Boc strategy) using an automated peptide synthesizer, in the presence of suitable resin. To attain the target peptide Pasireotide, any of the following sequences could be employed.

```
DTrp-Lys-Tyr(Bzl)-Phe-{4-(OCO-NH-CH2-CH2-NH2)Pro}-
Phg,

Phg-DTrp-Lys-Tyr(Bzl)-Phe-{4-(OCO-NH-CH2-CH2-NH2)
Pro},

{4-(OCO-NH-CH2-CH2-NH2)Pro}-Phg-DTrp-Lys-Tyr(Bzl)-
Phe,

Phe-{4-(OCO-NH-CH2-CH2-NH2)Pro}-Phg-DTrp-Lys-Tyr
(Bzl),

Tyr(Bzl)-Phe-{4-(OCO-NH-CH2-CH2-NH2)Pro}-Phg-DTrp-
Lys,
and

Lys-Tyr(Bzl)-Phe-{4-(OCO-NH-CH2-CH2-NH2)Pro}-Phg-
DTrp
```

Thus the above 6 amino acid sequence yields respective linear peptide chains. The peptide chain is either cleaved from resin using suitable reagent, deprotected and then cyclized or first cyclized followed by removal of protecting groups.

Therefore, the process of US publication number 20110663260, essentially involves usage of amino acid proline substituted with an ethylene diamine at the '4' position. This would sterically hinder the peptide formation and thereby suffers in low peptide yield.

OBJECT OF THE INVENTION

In one object, the present invention provides a process for the preparation of Pasireotide of formula 11 which is Cyclo [Phe-{4-(OCO—NH—CH₂—CH₂—NH₂)Pro}-Phg-DTrp-Lys-Tyr(Bzl)].

In another object the present invention provides a novel intermediate compound of formula 8.

In another object the present invention provides a process for the preparation a novel intermediate compound of formula 8.

In another object, the present invention provides a process for the preparation of Pasireotide of formula 11 from the intermediate compound of formula 8.

Yet in another object, the present invention provides an improved process for the preparation of Pasireotide side chain Fmoc-(2S,4R)-(-4-O—CO—NH—CH₂—CH₂—NH-Boc)-Pro-OH.

SUMMARY OF THE INVENTION

Accordingly, the present invention provides processes for preparation of Pasireotide, its novel intermediate and process for said intermediate as shown in Scheme-1 and Scheme-2.

In one aspect the present invention provides a process for the preparation of Pasireotide of formula 11 [Cyclo [Phe-{4-(OCO—NH—CH₂—CH₂—NH₂)Pro}-Phg-DTrp-Lys-Tyr(Bzl)]], comprising the steps of:

a) coupling an intermediate compound of formula 8 with ethylene diamine side chain compound of formula 9 in presence of a coupling agent to give a compound of formula 10;

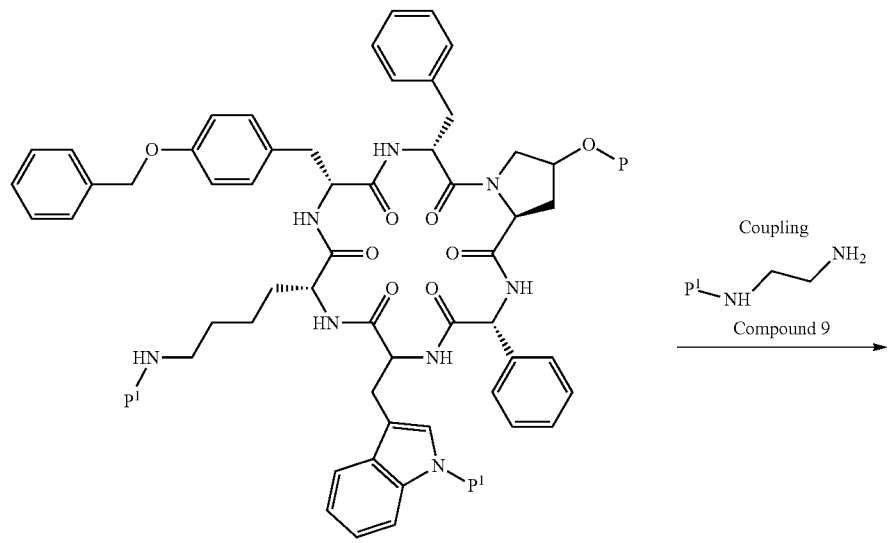

Compound 8
Where P is hydrogen or hydroxyl protecting group
and P¹ is amino protecting group

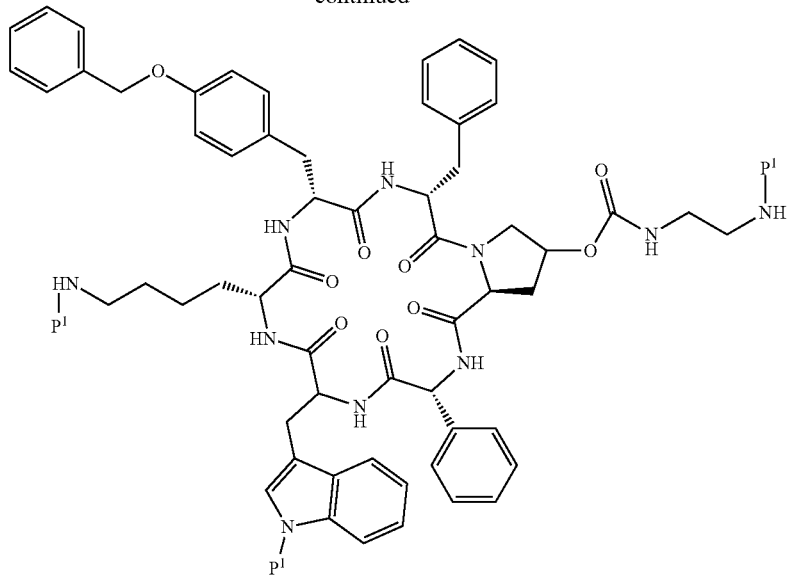
Compound 10
b) deprotecting the protecting groups from the peptide compound of formula 10 obtained in step (a) to obtain crude Pasireotide (11);
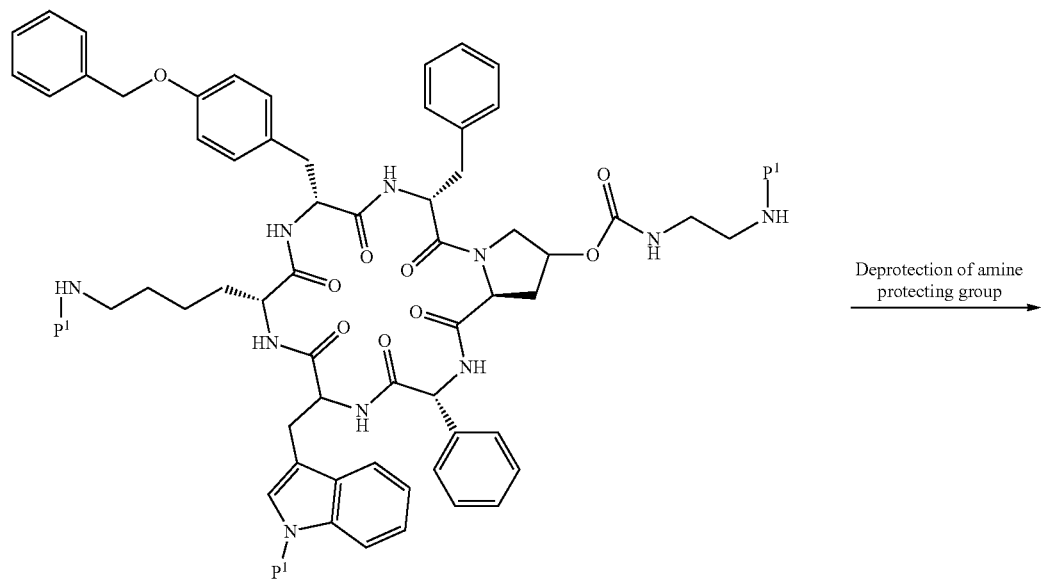
Compound 10
Deprotection of amine protecting group →

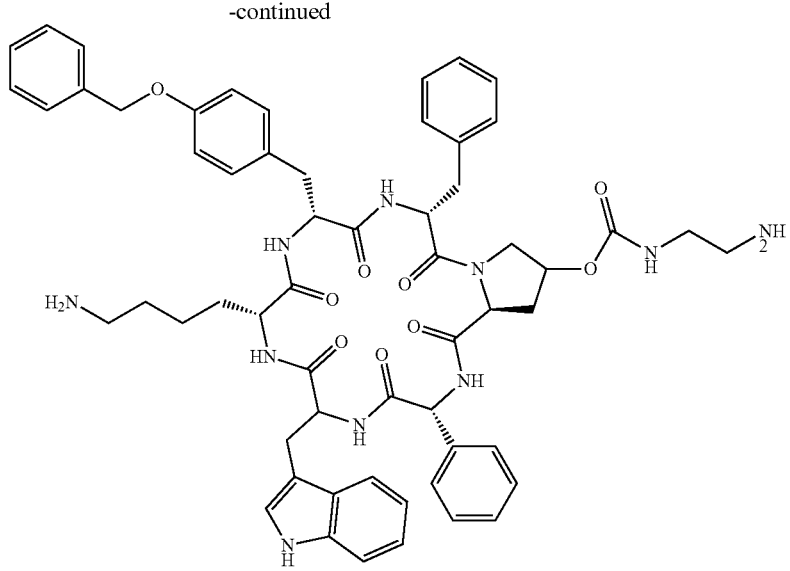

Compound 11
Pasireotide c) optionally, purifying crude Pasireotide (11) by preparative HPLC; and
d) optionally, isolation of pure Pasireotide (11) or its pharmaceutically acceptable salt form.

The said hydrogen or hydroxyl protecting group "P" is selected from the group comprising of dimethoxy trityl (DMT), Methoxytrityl (MMT), Trityl (Trt), tert-butyl and t-butyloxy carbonyl; and the said amino protecting group "$P^1$" is selected from the group comprising of 9-fluorenyln ethoxycarbonyl (Fmoc), tert-butyloxycarbonyl (Boc), Benzyloxycarbonyl (Cbz) and 2-(4-biphenyl)-2-propyloxycarbonyl (Bpoc). Preferably the amino protecting group is tert-butyloxycarbonyl (Boc).

The coupling agent in step (a) is selected from the group comprising of phosgene, carbonyldiimidazole (CDI), Hydroxy benzotriazole (HOBt), O-(benzotriazol-1-yl)-N,N,N',N'-tetramethyluronium tetrafluoroborate (TBTU), 1,3-dicyclohexylcarbodiimide (DCC), Diisopropylcarbodiimide (DIC), O-Benzotriazole-N,N,N',N-tetramethyluroniumhexafluorophosphate (HBTU), Benzotriazol-1-yl-oxy-tris(dimethylamino)phosphonium hexafluorophosphate (BOP), Benzotriazol-1-yloxy tri(pyrrolidino)phosphonium hexafluorophosphate (PyBOP), (Bromotri(pyrrolidino)phosphonium hexafluorophosphate (PyBrOP), Chlorotri(pyrrolidino) phosphonium hexafluorophosphate (PyClOP), Ethyl-2-cyano-2-(hydroxyimino)acetate (Oxyma Pure), O-(6-Chlorobenzotriazol-1-yl)-1,1,3,3-tetramethyluronium tetrafluoroborate (TCTU), Ethyl 1,2-dihydro-2-ethoxyquinoline-1-carboxylate (EEDQ), 1-Cyano-2-ethoxy-2-oxoethylenaminooxy)dimethylaminomorpholino carbenium hexafluorophosphate (COMU), 3-(Diethoxy-phosphoryloxy)-3H-benzo[d][1,2,3] triazin-4-one (DEPBT), 1-hydroxy-1-7-azabenzotriazole (HoAt), 1-[Bis(dimethylamino)methylene]-1H-1,2,3-triazolo[4,5-b]pyridinium 3-oxide hexafluorophosphate (HATU) and dimethylamino(triazolo[4,5-b]pyridin-3-yloxy)methylidene]-dimethylazanium tetra fluoroborate (TATU) or a mixture thereof. Preferably the coupling agent is triphosgene or carbonyldiimidazole (CDI).

The coupling reaction of step (a) is carried out in presence of a solvent selected from the group comprising of N,N-dimethylformamide (DMF), Dichloromethane (DCM), Tetrahydrofuran (THF), N-Methyl pyrrolidine (NMP), Dimethylacetamide (DMAC) or a mixture thereof. Preferably the solvent is Dichloromethane (DCM) or Tetrahydrofuran (THF).

The deprotection in step (b) is carried out with a mixture of deprotecting reagents selected from the group comprising of Trifluoro acetic acid (TFA), Acetic acid, Triethyl silane (TES), Triisopropyl silane (TIS), Dithiothreitol (DTT), Ethanedithiol (EDT), ammonium iodide, acetyl cysteine, Dimethyl sulfide (DMS), phenol, cresol and thiocresol. Preferably the deprotecting reagent is a mixture of Trifluoroacetic acid (TFA) and Triisopropyl silane (TIS) in water.

In another aspect, the present invention provides a compound of formula 8

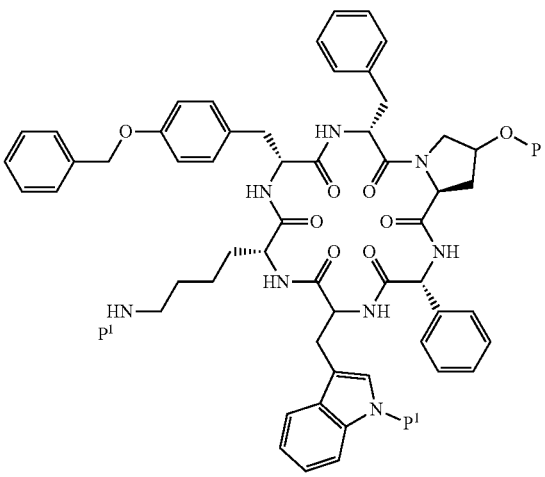

Compound 8 wherein, P and $P^1$ are as defined above.

In another aspect the present invention provides a process for preparation of above said compound of formula 8, comprising the steps of:
(a) loading a first amino acid Fmoc-Tyr(Bzl)-OH on Chlorotrityl resin to obtain Fmoc-Tyr(Bzl)-CTC resin using manual or automatic solid phase synthesizer;
(b) synthesizing Fmoc-Phe-Pro(4-OP)-Phg-DTrp($P^1$)-Lys($P^1$)-Tyr(Bzl)-CTC resin by coupling the Fmoc-Lys($P^1$)—OH, Fmoc-DTrp($P^1$)—OH, Fmoc-Phg-OH, Fmoc-Pro(4-OP)—OH and Fmoc-Phe-OH amino acids in the desired sequence;
(c) cleaving peptide resin from the desired peptide sequences, followed by cyclization to obtain cyclo (Phe-Pro(4-OP)-Phg-DTrp($P^1$)-Lys($P^1$)-Tyr(Bzl)) of compound 8;

wherein in step (c) any of the following desired peptide sequences can be followed to arrive at said desired cyclic peptide compound of formula 8:

```
DTrp(P¹)-Lys(P¹)-Tyr(Bzl)-Phe-{4-(OP)Pro}-Phg,

Phg-DTrp(P¹)-Lys(P¹)-Tyr(Bzl)-Phe-{4-(OP)Pro},

{4-(OP)Pro}-Phg-DTrp(P¹)-Lys(P¹)-Tyr(Bzl)-Phe,

Phe-{4-(OP)Pro}-Phg-DTrp(P¹)-Lys(P¹)-Tyr(Bzl),

Tyr(Bzl)-Phe-{4-(OP)Pro}-Phg-DTrp(P¹)-Lys(P¹),
and

Lys(Boc)-Tyr(Bzl)-Phe-{4-(OP)Pro}-Phg-DTrp(P¹).
```

In another aspect, the present invention provides a process for preparation of above said compound of formula 8, comprising the steps of:

(a) coupling a compound of formula 1 with Fmoc-Tyr(Bzl)-OH in presence of coupling agent and solvent to give compound of formula 2;

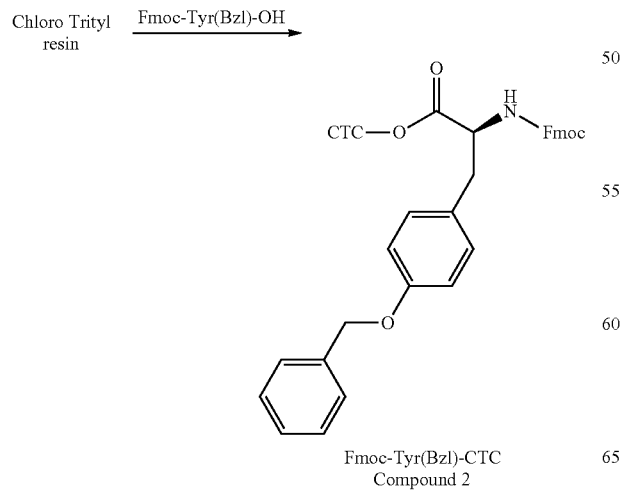

Fmoc-Tyr(Bzl)-CTC
Compound 2

(b) deblocking Fmoc and then coupling the compound of formula 2 with Fmoc-Lys($P^1$)—OH in presence of coupling agent and solvent to give compound of formula 3;

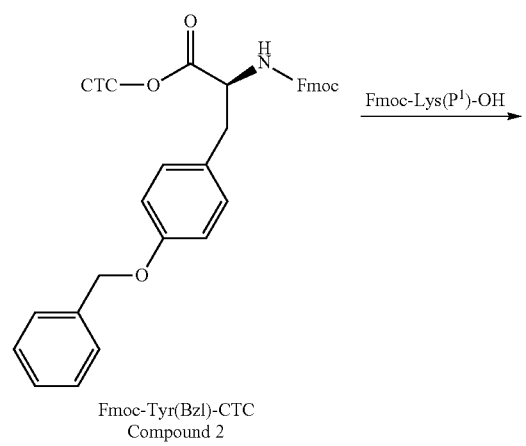

Fmoc-Tyr(Bzl)-CTC
Compound 2

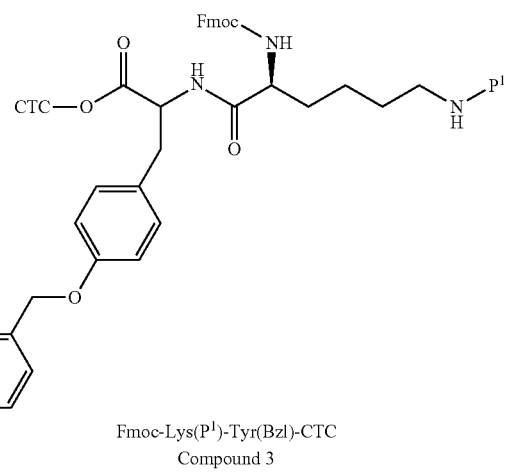

Fmoc-Lys($P^1$)-Tyr(Bzl)-CTC
Compound 3

(c) deblocking Fmoc and then coupling the compound of formula 3 with Fmoc-D-Trp($P^1$)—OH in presence of coupling agent and solvent to compound of formula 4;

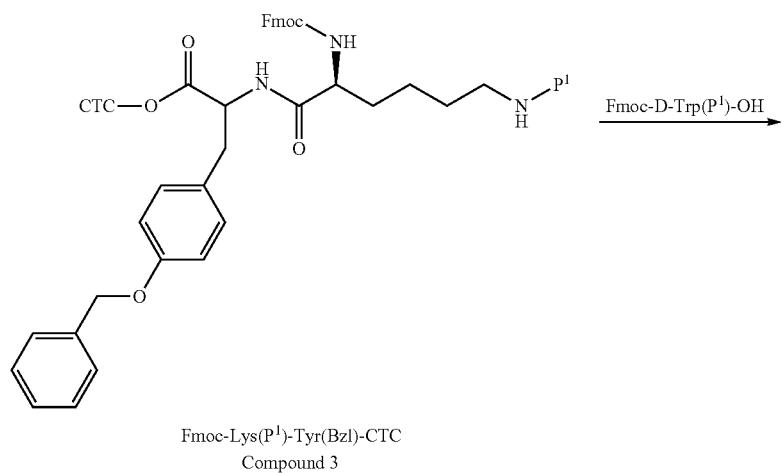
Fmoc-Lys(P¹)-Tyr(Bzl)-CTC
Compound 3
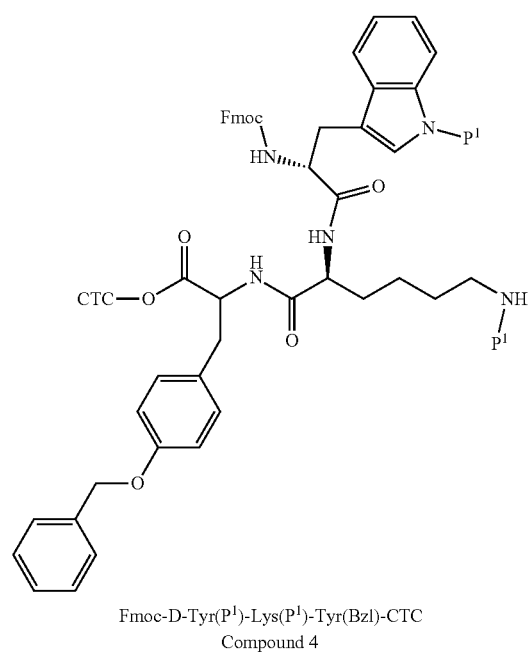
Fmoc-D-Tyr(P¹)-Lys(P¹)-Tyr(Bzl)-CTC
Compound 4

(d) deblocking Fmoc and then coupling the compound of formula 4 with Fmoc-Phg-OH in presence of coupling agent and solvent to give compound of formula 5;

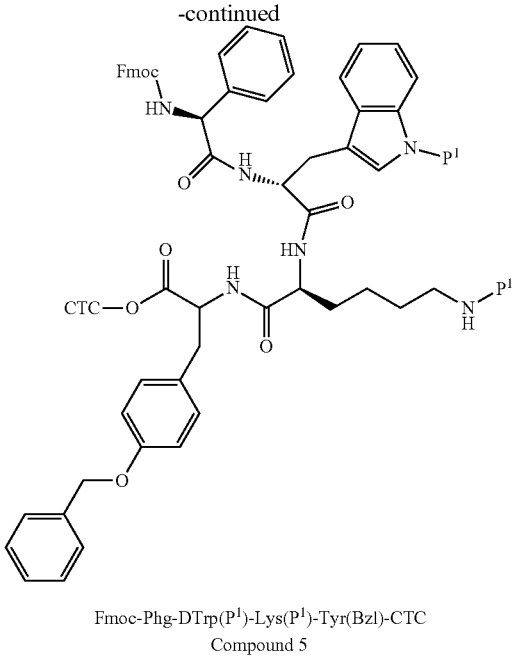

Fmoc-Phg-DTrp(P¹)-Lys(P¹)-Tyr(Bzl)-CTC
Compound 5

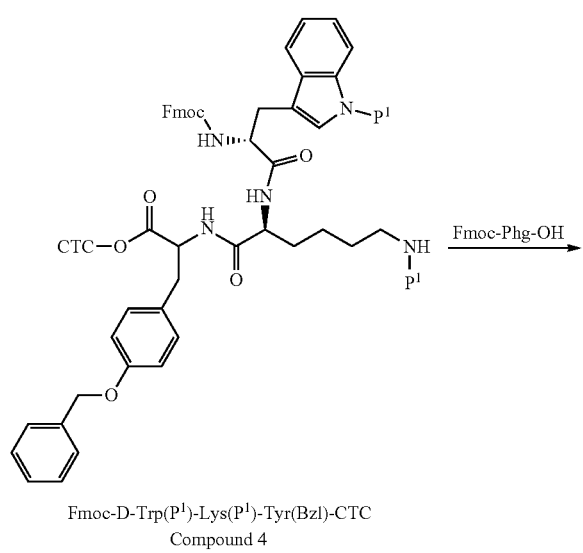

Fmoc-D-Trp(P¹)-Lys(P¹)-Tyr(Bzl)-CTC
Compound 4

→ Fmoc-Phg-OH (e) deblocking Fmoc and then coupling the compound of formula 5 with Fmoc-Pro(4-OP)—OH in presence of coupling agent and solvent to give compound of formula 6;

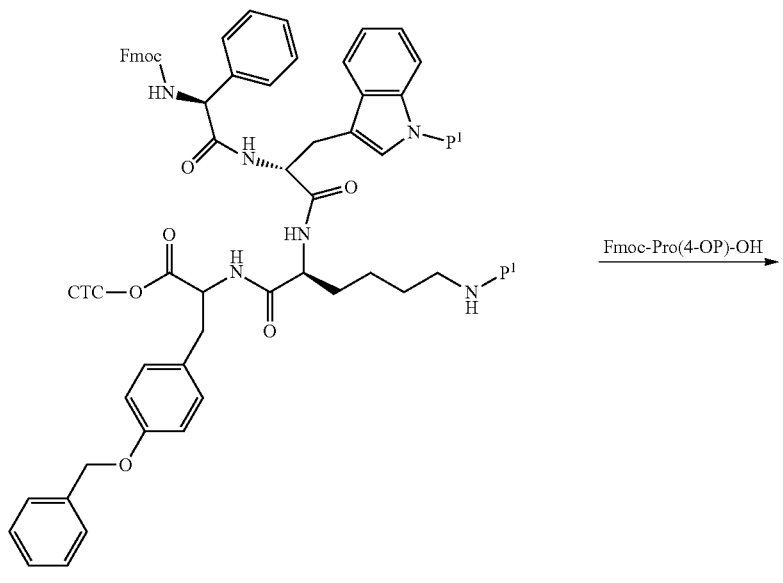

Fmoc-Phg-DTrp(P¹)-Lys(P¹)-Tyr(Bzl)-CTC
Compound 5

→ Fmoc-Pro(4-OP)-OH

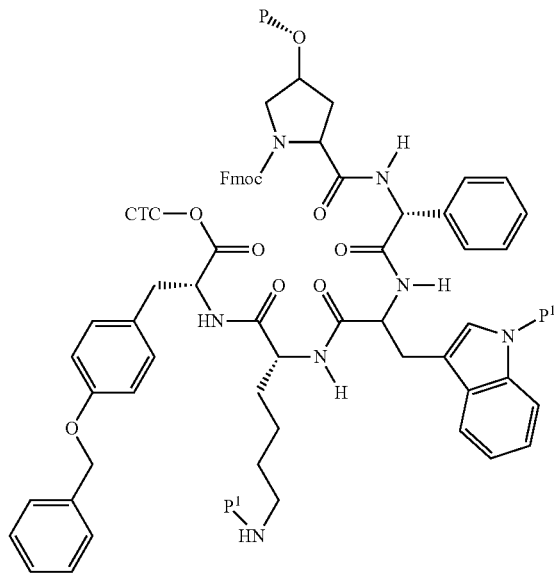

Fmoc-Pro(4-ODMT)-Phg-DTrp(P¹)-Lys(P¹)-Tyr(Bzl)-CTC
Compound 6

(f) deblocking Fmoc and then coupling the compound of formula 6 with Fmoc-Phe-OH in presence of coupling agent and solvent to give compound of formula 7;

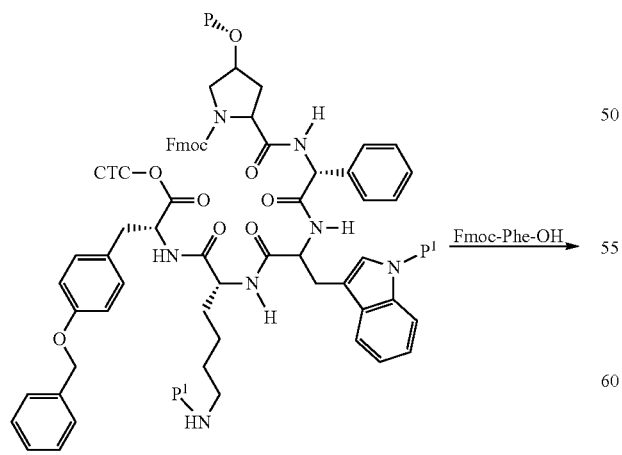

Fmoc-Pro(4-ODMT)-Phg-
DTrp(P¹)-Lys(P¹)-Tyr(Bzl)-CTC
Compound 6

→ Fmoc-Phe-OH

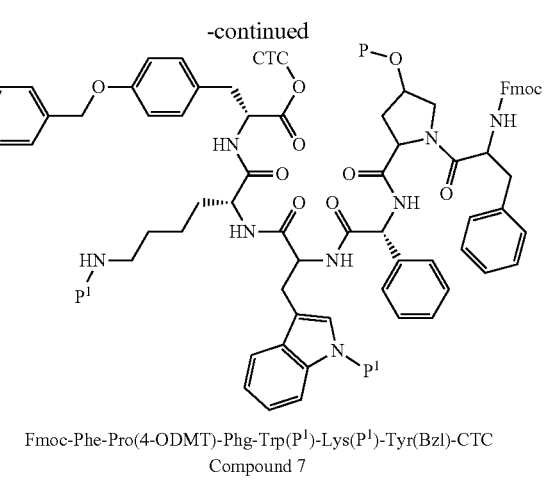

Fmoc-Phe-Pro(4-ODMT)-Phg-Trp(P¹)-Lys(P¹)-Tyr(Bzl)-CTC
Compound 7

(g) cleaving Fmoc from the compound of formula 7, followed by cyclization to give compound of formula 8.

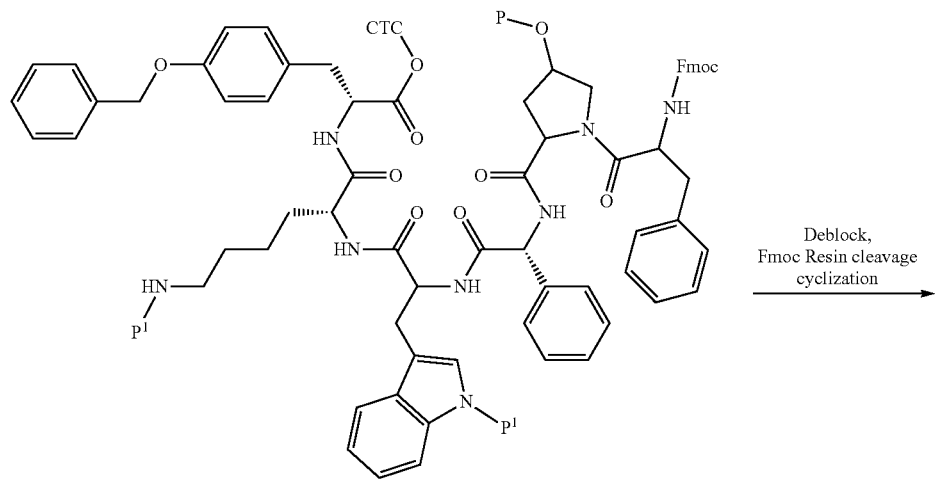

Fmoc-Phe-Pro(4-ODMT)-Phg-Trp($P^1$)-Lys($P^1$)-Tyr(Bzl)-CTC
Compound 7

Deblock,
Fmoc Resin cleavage
cyclization

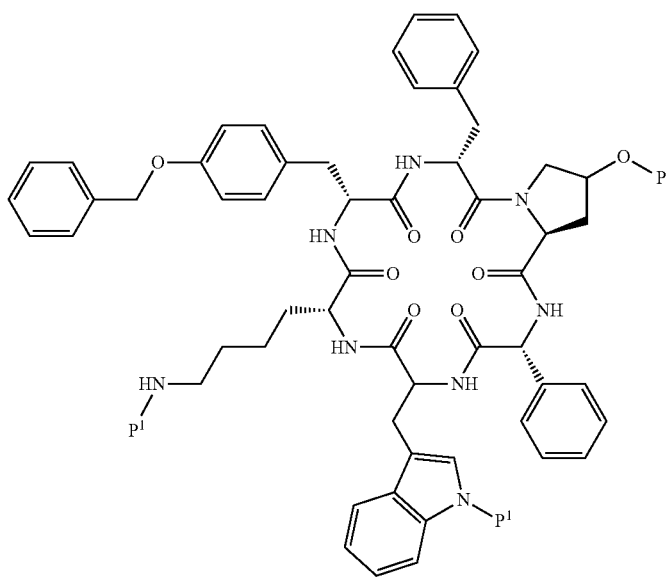

Compound 8 wherein, P and $P^1$ are as defined above.

In any of the above said processes for preparation of compound of formula 8, the coupling agent in any of the steps is selected from the group comprising of phosgene, carbonyldiimidazole (CDI), Hydroxy benzotriazole (HOBt), O-(benzotriazol-1-yl)-N,N,N',N'-tetramethyluronium tetrafluoroborate (TBTU), 1,3-dicyclohexylcarbodiimide (DCC), Diisopropylcarbodiimide (DIC), O-Benzotriazole-N,N, N' N-tetramethyluroniumhexafluoro phosphate (HBTU), Benzotriazol-1-yl-oxy-tris(dimethylamino)phosphonium hexafluorophosphate (BOP), Benzotriazol-1-yloxy tri(pyrrolidino)phosphonium hexafluorophosphate (PyBOP), (Bromotri(pyrrolidino) phosphonium hexafluorophosphate (PyBrOP), Chlorotri(pyrrolidino)phosphonium hexafluorophosphate (PyClOP), Ethyl-2-cyano-2-(hydroxyimino) acetate (Oxyma Pure), O-(6-Chlorobenzotriazol-1-yl)-1,1,3,3-tetramethyluronium tetrafluoroborate (TCTU), Ethyl 1,2-dihydro-2-ethoxyquinoline-1-carboxylate (EEDQ), 1-Cyano-2-ethoxy-2-oxoethyHdenaminooxy) dimethylaminomorpholino carbenium hexafluorophosphate (COMU), 3-(Diethoxy-phosphoryloxy)-3H-benzo[d][1,2,3] triazin-4-one (DEPBT), 1-hydroxy-7-azabenzotriazole (HoAt), 1-[Bis(dimethylamino)methylene]-1H-1,2,3-triazolo[4,5-b]pyridinium 3-oxide hexafluorophosphate (HATU) and dimethylamino(triazolo[4,5-b]pyridin-3-yloxy)methylidene]-dimethylazanium tetra fluoroborate (TATU) or a mixture thereof.

The solvent in any of the steps is selected from the group comprising of N,N-dimethylformamide (DMF), Dichloromethane (DCM), Tetrahydrofuran (THF), N-Methyl pyrrolidine (NMP), Dimethylacetamide (DMAC) or a mixture thereof.

In another aspect, the present invention provides a process for the preparation of Pasireotide of formula (11) comprising the steps of:
(a) treating 2-chloro Trityl Resin (CTC Resin) with Fmoc-Tyr(Bzl)-OH in presence of DCM and N,N-diisopropylethylamine (DIPEA) to obtain Fmoc-Tyr(Bzl)-Chloro Trityl resin;
(b) coupling of Fmoc-Lys(Boc)-OH with Fmoc-Tyr(Bzl)-resin in presence of coupling agents HOBt and HBTU, in presence of solvent DMF and in presence of N,N-diisopropyl ethyl amine (DIEA) to obtain Fmoc-Lys(Boc)-Tyr(Bzl)-resin;
(c) coupling of Fmoc-D-Trp(Boc)-OH with Fmoc-Lys(Boc)-Tyr(Bzl)-resin in presence of coupling agents HOBT and TBTU in DMF and in presence of N,N-diisopropyl ethylamine to obtain Fmoc-D-Trp(Boc)-Lys(Boc)-Tyr(Bzl)-resin;
(d) coupling of Fmoc-Phg-OH with Fmoc-D-Trp(Boc)-Lys(Boc)-Tyr(Bzl)-resin in presence of coupling agents HOAT and DIC in DMF and in presence of N-Methyl morpholine (NMM) to obtain Fmoc-Phg-D-Trp(Boc)-Lys(Boc)-Tyr(Bzl)-resin;
(e) coupling of Fmoc-Pro(4-OP)—OH with Fmoc-Phg-D-Trp(Boc)-Lys(Boc)-Tyr(Bzl)-CTC-resin in presence of coupling agents HOBT and DIC in DMF and in presence of N-Methyl morpholine (NMM) to obtain Fmoc-Pro (4-OP)-Phg-D-Trp(Boc)-Lys(Boc)-Tyr(Bzl)-CTC resin;
(f) coupling of Fmoc-Phe-OH with Pro(4-OP)-Phg-D-Trp(Boc)-Lys(Boc)-Tyr(Bzl)-CTC resin in presence of coupling agents HBTU and HOBT in DMF and in presence of N,N-diisopropyl ethylamine (DIEA) to obtain Fmoc-Phe-Pro(4-OP)-Phg-D-Trp(Boc)-Lys(Boc)-Tyr(Bzl)-CTC resin;
(g) cleavage of resin from Fmoc-Phe-Pro(4-OP)-Phg-D-Trp(Boc)-Lys(Boc)-Tyr(Bzl)-CTC resin using TFA in DCM followed by neutralization by using DIPEA in DCM to obtain a solid HPhe-Pro(4-OH)Phg-D-Trp(Boc)-Lys(Boc)-Tyr(Bzl)-OH;
(h) cyclization of H-Phe-Pro (4-OP)-Phg-D-Trp(Boc)-Lys(Boc)-Tyr(Bzl)-OH in presence of HATU and HOAT in DMF and in presence of N,N-diisopropyl ethyl amine (DIEA) to obtain cyclo(Phe-Pro (4-OH)-Phg-D-Trp(Boc)-Lys(Boc)-Tyr(Bzl)) of compound 8;
(i) coupling of Cyclo (Phe-Pro(4-OP)-Phg-D-Trp(Boc)-Lys(Boc)-Tyr(Bzl)) compound 8 with N-Boc diaminoethane in presence of coupling agent triphosgene in THF to give chlorocarbonate intermediate;
(j) deprotecting the amine protecting groups by treating with TFA/TIS and water to give crude Pasireotide;
(k) optionally, purifying crude Pasireotide as obtained above by preparative HPLC and further converting into Pasireotide salt by treating with desired acid.

In another aspect, the present invention provides a process for the preparation of Pasireotide of formula (11) comprising the steps of:
(a) treating 2-chloro trityl resin (CTC-resin) with Fmoc-Phe-OH in dichloromethane and N, N-diisopropylethyl amine to obtain Fmoc-Phe-CTC resin;
(b) coupling Fmoc-Phe-CTC resin with Fmoc-Tyr(Bzl)-OH in presence of HOBt in dimethyl formamide and in presence of N'-Diisopropylcarbodiimide (DIDC) to obtain Fmoc-Tyr(Bzl)-Phe-CTC resin;
(c) coupling Fmoc-tyr(Bzl)-Phe-CTC resin with Fmoc-Lys(Boc)-OH in presence of HOBt in DMF and in presence of N,N-diisopropyl carbodiimide to obtain Fmoc-Lys(Boc)-Tyr(Bzl)-Phe-CTC resin;
(d) coupling of Fmoc-D-Trp(Boc)-OH with Fmoc-Lys(Boc)-Tyr(Bzl)-Phe-CTC resin in presence of HOBt in DMF and in presence of N,N-diisopropyl carbodiimide to obtain Fmoc-D-Trp(Boc)-Lys(Boc)-Tyr(Bzl)-Phe-CTC resin;
(e) coupling of Fmoc-Phg-OH with Fmoc-D-Trp(Boc)-Lys(Boc)-Tyr(Bzl)Phe-CTC Resin in presence of HOBt and DIC in DMF to obtain Fmoc-phg-D-Trp(Boc)-Lys(Boc)-Tyr(Bzl)-Phe-CTC resin;
(f) coupling of Fmoc-Pro-OH with Fmoc-Phg-D-Trp(Boc)-Lys(Boc)-Tyr(Bzl)-Phe-CTC resin in presence of HOBt and DIC in DMF to obtain Fmoc-Pro-Phg-D-Trp(Boc)-Lys(Boc)-Tyr(Bzl)-Phe-CTC Resin;
(g) cleaving of resin from Fmoc-Pro-Phg-D-Trp(Boc)-Lys(Boc)-Tyr(Bzl)-Phe-CTC Resin by treating with TFA in DCM followed by neutralization with DIPEA in DCM to obtain resin de protected Pro-Phg-D-Trp(Boc)-Lys(Boc)-Tyr(Bzl)-Phe;
(h) cyclization of H-Pro-Phe-Phg-D-Trp(Boc)-Lys(Boc)-Tyr(Bzl)-Phe-OH in presence of dichloromethane, TBTU and N,N-diisopropylethylamine to obtain cyclo[Pro(4-OH)-Phg-D-Trp(BocO-lys(Boc)-Tyr(Bzl)-Phe];
(i) coupling of cyclo[Pro(4-OH)-Phg-D-Trp(Boc-lys(Boc)-Tyr(Bzl)-Phe] compound 8 with Boc protected Ethylene diamine in dichloromethane solvent using carbonyl diimidazole and 4-(dimethyl amino) pyridine to get cyclo(Pro(4-OCO—NH—CH2-CH2-NH-Boc)-Phg-D-Trp(Boc)-Lys(Boc)-Tyr(Bzl)-Phe];
(j) deprotection of Boc group of cyclo(Pro(4-OCO—NH—CH2-CH2-NH-Boc)-Phg-D-Trp(Boc)-Lys(Boc)-Tyr(Bzl)-Phe] by treating with TFA/Tis/water to give crude Pasireotide;
(k) optionally purifying crude Pasireotide as obtained above by preparative HPLC to obtain Pasireotide with 99.9% purity.

In a further aspect, the present invention provides an improved process for the preparation of Pasireotide side chain Fmoc-(2S,4R)-(4-OCO—NH—CH2-CH2-NH-Boc)-Pro-OH, comprising the steps of:
(a) treating solution of Fmoc-hydroxyl proline in methanol with thionyl chloride to get Fmoc-hydroxy proline methyl ester;
(b) treating solution of Fmoc-hydroxy proline methyl ester in dichloromethane with DMAP and CDI and then charging Boc protected ethylene diamine to get Fmoc-(2S, 4R)-4(-OCO—NH—CH2-CH2-NH-Boc-Pro-OMe;
(c) hydrolyzing Fmoc-(2S, 4R)-4(-OCO—NH—CH2-CH2-NH-Boc-Pro-OMe obtained in step (b) by treating with sodium hydroxide in a mixture of 1, 4-dioxane and water and providing a mixture of H-(2S,4R)-(4OCO—NH—$CH_2$—$CH_2$—NH-Boc)-Pro-OH and the desired product Fmoc-(2S,4R)-(4OCO—NH—$CH_2$—$CH_2$—NH-Boc)-Pro-OH.

DETAILED DESCRIPTION OF THE INVENTION

The present invention relates to a process for the preparation of Pasireotide of formula 11 Cyclo[Phe-{4-(OCO—NH—$CH_2$—$CH_2$—$NH_2$) Pro}-Phg-DTrp-Lys-Tyr(Bzl)], which comprises the following steps:
(a) preparation of intermediate compound 8 by coupling of suitable fragments of amino acids by solid phase synthesis;
(b) coupling of intermediate of compound 8 with ethylene diamine side chain in presence of coupling agents;

(c) deprotection of the protecting groups from peptide;
(d) purification of Pasireotide by preparative HPLC;
(e) isolation of pure Pasireotide or its pharmaceutically acceptable salt form.

In an embodiment, the present invention relates to a process for the preparation of novel intermediate of compound 8 by coupling of suitable amino acid fragments by solid phase synthesis followed by cyclization and isolation of compound 8. The six sequences in which the amino acids are reacted to form six linear peptides are:

DTrp(P¹)-Lys(P¹)-Tyr(Bzl)-Phe-{4-(O-P)Pro}-Phg,

Phg-DTrp(P¹)-Lys(P¹)-Tyr(Bzl)-Phe-{4-(O-P)Pro},

{4-(O-P)Pro}-Phg-DTrp(P¹)-Lys(P¹)-Tyr(Bzl)-Phe,

Phe-{4-(O-P)Pro}-Phg-DTrp(P¹)-Lys(P¹)-Tyr(Bzl),

Tyr(Bzl)-Phe-{4-(O-P)Pro}-Phg-DTrp(P¹)-Lys(P¹), and

Lys(P¹)-Tyr(Bzl)-Phe-{4-(O-P)Pro}-Phg-DTrp(P¹)

Wherein p represents hydrogen or hydroxyl protecting group and $P^1$ is an amino protecting group.

In an embodiment, the present invention relates to a process for the preparation of Pasireotide by coupling of protected intermediate of compound 8 with Ethylenediamine side chain in presence of coupling agent.

In yet another embodiment of the present invention, the compound 8 used for the preparation of Pasireotide is structurally represented as:

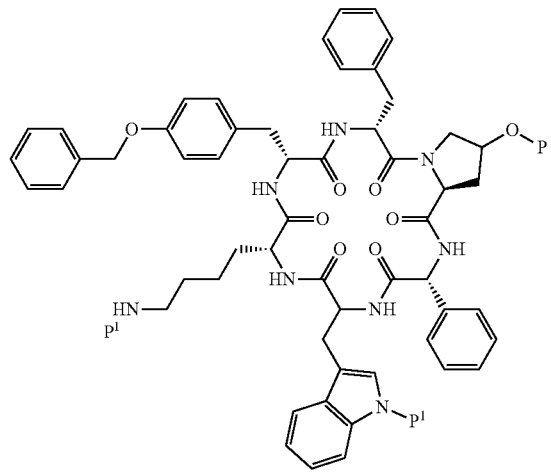

Compound 8

Wherein p represents hydrogen or hydroxyl protecting group and $P^1$ is an amino protecting group.

In an embodiment of the present invention, a process for the preparation of Pasireotide comprises of the following steps:

(a) Preparing intermediate of compound 8 using suitable fragments of amino acids by solid phase synthesis;
(b) Coupling of intermediate of compound 8 with protected ethylene diamine side chain in presence of coupling agents;
(c) Deprotection of the protecting groups from peptide;
(d) Purification of Pasireotide by Prep. HPLC;
(e) Isolation of pure Pasireotide or its salt form.

Method of synthesis of Pasireotide, according to the present invention is illustrated in the following Scheme-1.

SCHEME 1: SYNTHESIS OF PASIREOTIDE (11)

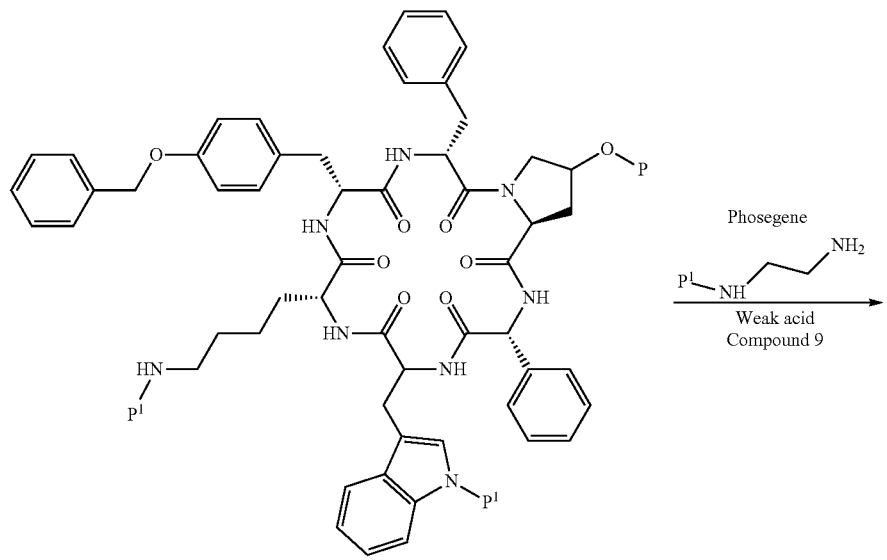

Compound 8
Where P is hydrogen or hydroxyl protecting group
and $P^1$ is amino protecting group

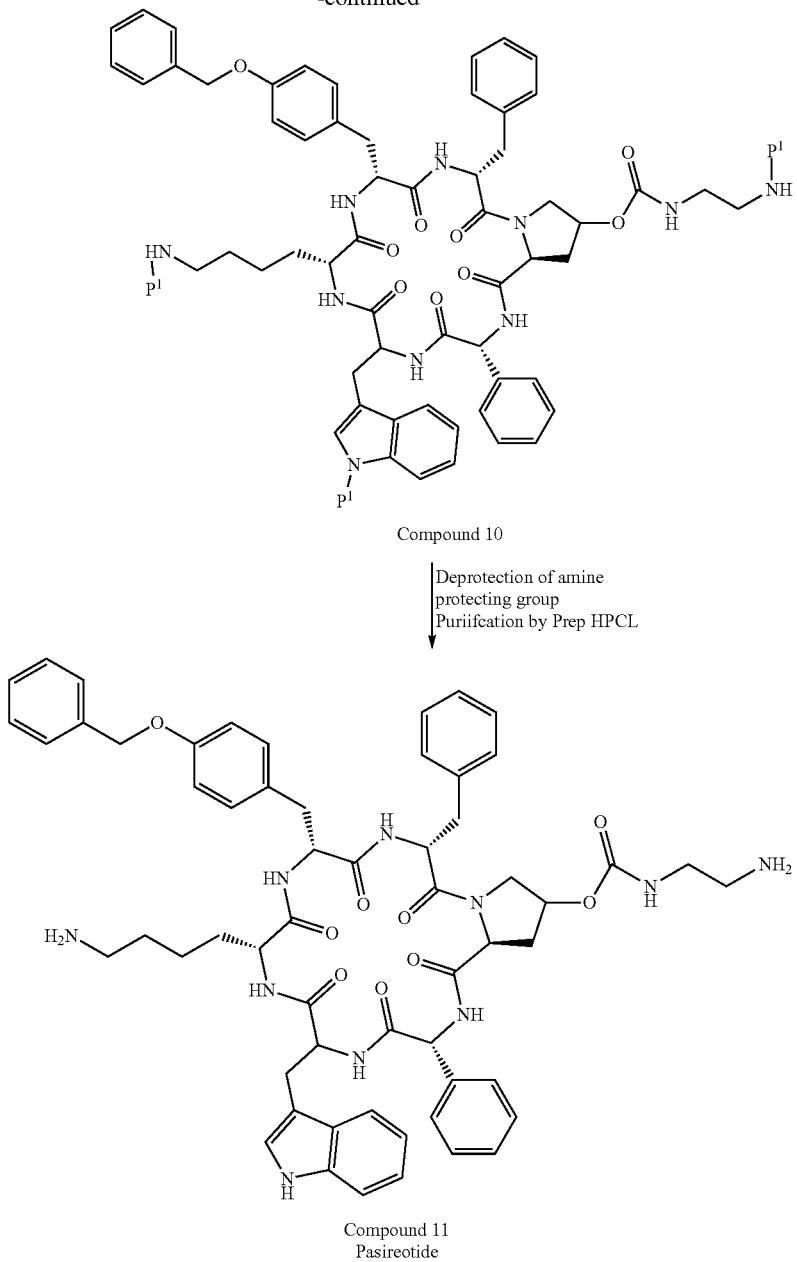

Compound 10

Deprotection of amine protecting group
Puriifcation by Prep HPCL

Compound 11
Pasireotide

Another embodiment of the present invention relates to synthesis of intermediate of compound 8 by sequential addition of amino acids to a solid support followed by cleavage of peptide resin and cyclization.

In yet another embodiment of the present invention relates to the synthesis of intermediate of compound 8 either by sequential addition of amino acids to a solid support or coupling of two suitable fragments using solid phase synthesis, cleavage of peptide resin and cyclization.

In another embodiment of the present invention relates to improved process for the preparation of side chain Fmoc-(2S,4R)-(4-O—CO—NH—CH2-CH2-NH-Boc)-Pro-OH, which is used as key intermediate in the synthesis of Passiontide.

Yet another embodiment of the present invention relates to the synthesis of intermediate of compound 8, which comprises the following steps:

(a) Loading first amino acid Fmoc-Tyr(Bzl)-OH on Chlorotrityl resin to obtain Fmoc-Tyr(Bzl)-CTC resin using manual or automatic solid phase synthesizer;

(b) Synthesizing Fmoc-Phe-Pro(4-OP)-Phg-DTrp($P^1$)-Lys($P^1$)-Tyr(Bzl)-CTC resin by coupling the Fmoc-Lys($P^1$)—OH, Fmoc-DTrp($P^1$)—OH, Fmoc-Phg-OH, Fmoc-Pro(4-OP)—OH and Fmoc-Phe-OH amino acids in the desired sequence;

(c) Cleave peptide resin from the desired peptide sequences as described below followed by cyclization to obtain cyclo(Phe-Pro(4-OP)-Phg-DTrp($P^1$)-Lys($P^1$)-Tyr(Bzl)) of compound 8.

Any of the following sequences can be followed to arrive at the desired cyclic peptide 8

```
DTrp(P¹)-Lys(P¹)-Tyr(Bzl)-Phe-{4-(OP)Pro}-Phg,

Phg-DTrp(P¹)-Lys(P¹)-Tyr(Bzl)-Phe-{4-(OP)Pro},

{4-(OP)Pro}-Phg-DTrp(P¹)-Lys(P¹)-Tyr(Bzl)-Phe,

Phe-{4-(OP)Pro}-Phg-DTrp(P¹)-Lys(P¹)-Tyr(Bzl),
```

-continued
```
Tyr(Bzl)-Phe-{4-(OP)Pro}-Phg-DTrp(P¹)-Lys(P¹),
and
Lys(Boc)-Tyr(Bzl)-Phe-{4-(OP)Pro}-Phg-DTrp(P¹)
```
Method of synthesis of compound 8, according to the present invention is illustrated in the following Scheme-2:
SCHEME-2: SYNTHESIS OF COMPOUND 8
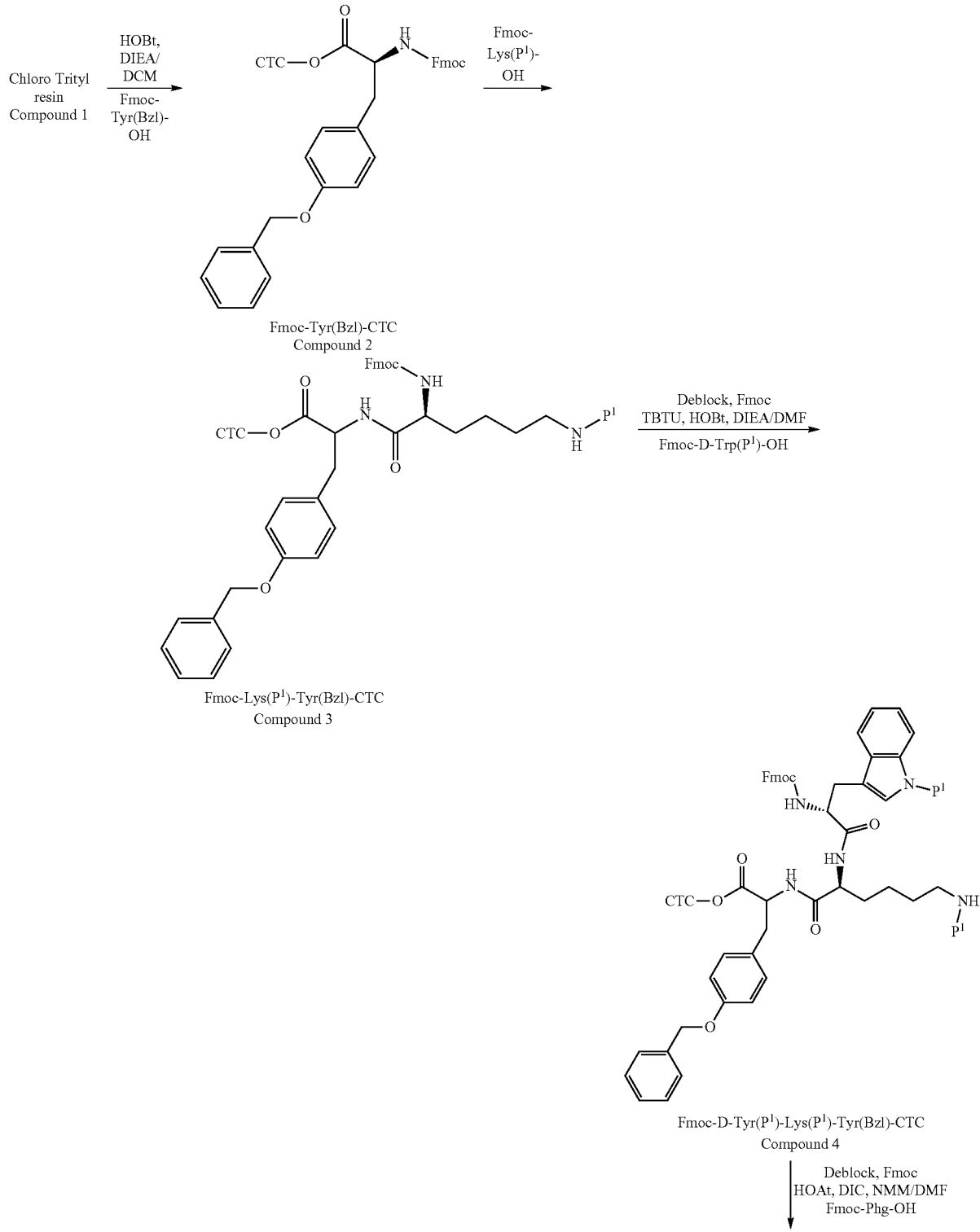

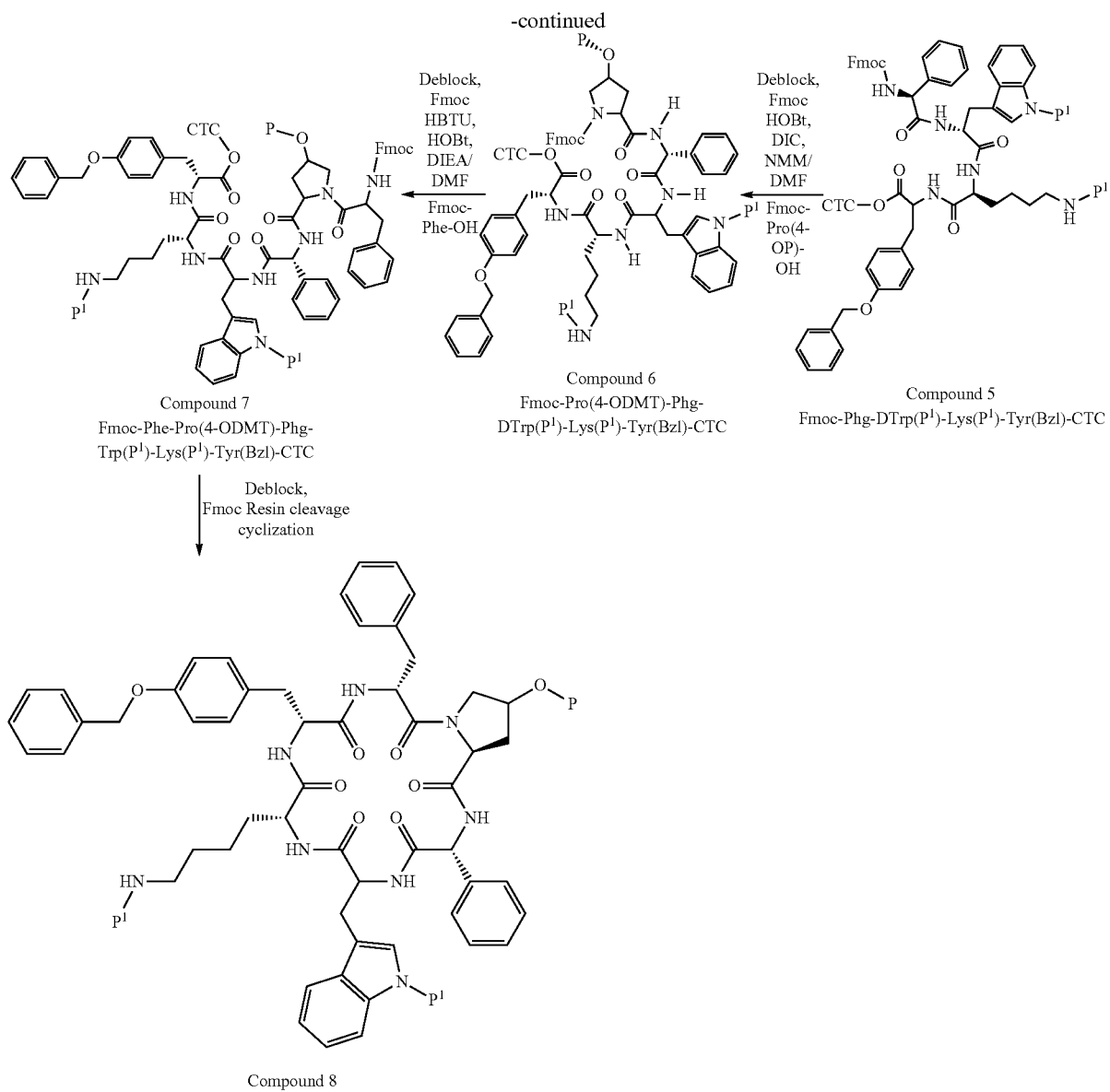

Compound 8
Where P is hydrogen or hydroxyl protecting group
and P¹ is an amino protecting group In yet another embodiment of the present invention the carboxyl, phenolic and alcoholic moieties are by protecting groups comprising DMT, MMT, Trt, tert-butyl, t-butoxy carbonyl and the like. Likewise, amino protecting group P¹ are selected from but not limited to a group comprising Fmoc, Boc, Cbz, Bpoc, and the like.

In another embodiment of the present invention the coupling agent are selected from the group consisting of HOBt, TBTU, DCC, DIC, HBTU, BOP, PyBOP, PyBrOP, PyClOP, Oxyma pure, TCTU, EEDQ, COMU, DEPBT, HoAt, HATU, TATU and the like, and mixtures thereof.

In another embodiment of the present invention the coupling takes place in one of the solvents selected from the group comprising of DMF, DCM, THF, NMP, DMAC or mixtures thereof.

In yet another embodiment of the present invention, the solid phase synthesis is carried out on an insoluble polymer which is acid sensitive. An acid sensitive resin selected from a group comprising trityl CTC, Wang Resin, 4-methyl trityl chloride and Sasrin.

In yet another embodiment of the present invention, the linear protected peptide is deprotected with a mixture of reagents selected from the group comprising of TFA, Acetic acid, TES, TIS, DTT, EDT, ammonium iodide, acetyl cysteine, DMS, phenol, cresol and thiocresol.

In an embodiment of the present invention, the resin cleavage agent is preferably a mixture of TFA and DCM or TFE, acetic acid mixed with DCM compound.

In an embodiment of the present invention, purification of Pasireotide is carried out by preparative HPLC.

In yet another embodiment of the present invention purification of Pasireotide is carried out by preparative HPLC using a mixture of solvents comprising TFA, water and acetonitrile and converting into pharmaceutically acceptable salt.

BRIEF DESCRIPTION OF ABBREVIATIONS

HBTU—O-Benzotriazole-N,N,N' N-tetramethyluroniumhexafluoro phosphate
HOBt—Hydroxy benzotriazole
TBTU—O-(benzotriazol-1-yl)-N,N,N',N'-tetramethyluronium tetrafluoroborate,
Cl-HOBt—6-chloro-1-hydroxy-benzotriazole
DCC—1,3-dicyclohexylcarbodiimide DIC—Diisopropylcarbodiimide
BOP—Benzotriazol-1-yl-oxy-tris(dimethylamino)phosphonium hexafluorophosphate
PyBOP—Benzotriazol-1-yloxy tri(pyrrolidino)phosphonium hexafluorophosphate
PyBrOP—Bromotri(pyrrolidino)phosphonium hexafluorophosphate
PyClOP—Chlorotri(pyrrolidino)phosphonium hexafluorophosphate (PyClOP),
Oxyma—Ethyl-2-cyano-2-(hydroxyimino) acetate (Oxyma Pure),
TCTU—O-(6-Chlorobenzotriazol-1-yl)-1,1,3,3-tetramethyluronium tetrafluoroborate
EEDQ—Ethyl 1,2-dihydro-2-ethoxyquinoline-1-carboxylate
COMU—1-Cyano-2-ethoxy-2-oxoethyHdenaminooxy) dimethylaminomorpholino carbenium hexafluorophosphate
HATU—1-[Bis(dimethylamino)methylene]-1H-1,2,3-triazolo[4,5-b]pyridinium-3-oxide hexa fluorophosphate
HOAt—1-hydroxy-7-azabenzotriazole
TATU—[dimethylamino(triazolo[4,5-b]pyridin-3-yloxy) methylidene]-dimethylazanium tetra fluoroborate
Oxyma—ethyl 2-cyano-2-(hydroxyimino)acetate
DIPEA—N,N-diisopropylethylamine (DIEA)
DMF—N,N-dimethylformamide
DCM—Dichloromethane
THF—Tetrahydrofuran
NMP—N-Methyl pyrrolidine
DMAC—Dimethylacetamide
TFA—Trifluoro acetic acid
EDT—Ethanedithiol
TIS—Triisopropyl silane
TES—Triethyl silane
DTT—Dithiothreitol
DMS—Dimethyl sulfide
DMSO—Dimethyl sulfoxide
MTBE—Methyl tert-butylether
MeOH—Methanol
IPA—Isopropyl alcohol
CTC—Chlorotrityl chloride
Trt—Trityl
Acm—Acetamidomethyl
StBu—S-tert-butylmercapto
Tmob—Trimethoxybenzyl
DMT—dimethoxy trityl
MMT—Methoxytrityl
Fmoc—9-fluorenyln ethoxycarbonyl
Boc—tert-butoxycarbonyl
Cbz—Benzyloxycarbonyl Bpco—2-(4-biphenyl)-2-propyloxycarbonyl
TACM—S-Trimethylacetamidomethyl
DEPBT—3-(Diethoxy-phosphoryloxy)-3H-benzo[d][1,2,3] triazin-4-one The following examples further illustrate the present invention, but should not be constructed in any way as to limit its scope.

Example 1: Process for the Preparation of Pasireotide Intermediate of Compound 8 (Wherein $P^1$ is Boc) and Pasireotide (11)

Step 1: Synthesis of Fmoc-Tyr(Bzl)-Chloro Trityl Resin 2-chloro Trityl Resin (CTC Resin) (10 g, 1.0 mmol/gm) is transferred to a peptide reaction vessel and swelled for 1 hr with dichloromethane. DCM is drained and washed 2 times with DCM. 12.34 g of Fmoc-Tyr(Bzl)-OH is weighed and dissolved in dry dichloromethane and N,N-diisopropylethylamine (9.0 ml) is added. The reaction mixture is stirred at 0-5° C. for 5 min and added to the above resin and continued stirring for 2 hrs. Methanol (8.0 ml) is added and stirred for another 15 min; the solution is drained out and the resin is washed with 1% DIPEA in DCM.

The peptide resin was dried under vacuum and checked the loading of the $1^{st}$ residue attachment by UV spectrophotometer Step 2: Coupling of Fmoc-Lys(Boc)-OH to Fmoc-Tyr(Bzl)-resin The Fmoc group was deblocked by using 20% piperidine in DMF for about 20 min and the resin is washed with DMF and DCM alternatively 3 times. 9.5 g of Fmoc-Lys(Boc)-OH, 3.4 g of HOBT and 9.6 g of HBTU in DMF is dissolved and cooled to 0-5° C., N,N-diisopropyl ethyl amine (7 ml) is added. The mixture is activated for about 10 min and added to the above deprotected resin. The mixture is stirred for 2 hrs, the amino acid content is checked by Kaiser test and washed with DMF, IPA DCM and DMF to obtain Fmoc-Lys(Boc)-Tyr(Bzl)-resin. (BOC is used as the amine protecting group)

Step 3: Coupling of Fmoc-D-Trp(Boc)-OH to Fmoc-Lys(Boc)-Tyr(Bzl)-resin

The Fmoc group was deblocked by adding 20% piperidine in DMF to Fmoc-Lys(Boc)-Tyr(Bzl)-resin for about 20 min and the resin is washed with DMF and DCM alternatively 3 times. 10.5 g of Fmoc-D-Trp(Boc)-OH, 3.4 g of HOBT and 6.3 g of TBTU in DMF is dissolved and cooled to 0-5° C., then added N,N-diisopropyl ethylamine. The reaction mixture is activated for about 10 min and added to the above deprotected resin. The mixture is stirred for 2-3 hr, followed by washing with DMF, IPA, DCM and DMF. The amino acid content is checked by Kaiser test to obtain Fmoc-D-Trp(Boc)-Lys(Boc)-Tyr(Bzl)-resin.

Step 4: Coupling of Fmoc-Phg-OH to Fmoc-D-Trp(Boc)-Lys(Boc)-Tyr(Bzl)-resin

The Fmoc group was deblocked by using 20% piperidine in DMF from Fmoc-D-Trp(Boc)-Lys(Boc)-Tyr(Bzl)-resin for about 20 min and the resin is washed with DMF and DCM alternatively 3 times. 7.5 g of Fmoc-Phg-OH and 3.4 g of HOAT are dissolved in DMF and cooled to 0-5° C., then added 6.2 ml of DIC. The mixture is activated for about 10 min and added to the above deprotected resin. The reaction mixture is stirred for 15 minutes and N-Methyl morpholine (0.25 ml) is added to it. It is stirred for 2-3 hrs and the mixture is washed with DMF, IPA DCM and DMF. The amino acid content is checked by Kaiser test to obtain Fmoc-Phg-D-Trp(Boc)-Lys(Boc)-Tyr(Bzl)-resin.

Step 5: Coupling of Fmoc-Pro(4-OP)—OH to Fmoc-Phg-D-Trp(Boc)-Lys(Boc)-Tyr(Bzl)-CTC-resin The Fmoc group was deblocked by using 20% piperidine in DMF for about 20 min from Fmoc-Phg-D-Trp(Boc)-Lys(Boc)-Tyr(Bzl)-CTC-resin and the resin was washed with DMF and DCM alternatively 3 times. The required quantities of Fmoc-Pro(4-OP)—OH and 3.4 g of HOBT in DMF was dissolved and cool to 0-5° C., then add 6.2 ml of DIC. The mixture was activated for about 10 min and added to the above deprotected resin. Stirred for 15 minutes, and N-Methyl morpholine (0.25 ml) was added and stirred the mixture for 2-3 hrs, followed by washing with DMF, IPA DCM and DMF. The amino acid content is checked by Kaiser test to obtain Fmoc-Pro (4-OP)-Phg-D-Trp(Boc)-Lys (Boc)-Tyr(Bzl)-CTC resin.

Step 6: Coupling of Fmoc-Phe-OH to Pro(4-OP)-Phg-D-Trp(Boc)-Lys(Boc)-Tyr(Bzl)-CTC Resin The Fmoc group is deblocked by using 20% piperidine in DMF for about 20 min from Pro(4-ODMT)-Phg-D-Trp (Boc)-Lys(Boc)-Tyr(Bzl)-CTC resin and the resin is washed with DMF and DCM alternatively 3 times. 7.75 g of Fmoc-Phe-OH, 7.5 g of HBTU and 3.4 g of HOBT are dissolved in DMF and cool to 0-5° C., then added 7 ml of N,N-diisopropyl ethylamine. The mixture was activated for about 10 min and added to the above deprotected resin. The mixture was stirred for 2-3 hrs, followed by washing with DMF, IPA DCM and DMF. The amino acid content is checked by Kaiser test to obtain Fmoc-Phe-Pro(4-OP)-Phg-D-Trp(Boc)-Lys(Boc)-Tyr(Bzl)-CTC resin.

Step 7: Cleavage of Resin from Fmoc-Phe-Pro(4-OP)-Phg-D-Trp(Boc)-Lys(Boc)-Tyr(Bzl)-CTC Resin Fmoc group is deblocked by using 20% piperidine in DMF for about 20 min from Fmoc-Phe-Pro (4-OP)-Phg-D-Trp(Boc)-Lys(Boc)-Tyr(Bzl)-OH and the resin is washed with DMF and DCM alternatively 3 times and washed three times with methanol then completely dried under vacuum for about 3-4 hrs. This cleavage of peptide resin from HPhe-Pro(4-ODMT)-Phg-D-Trp(Boc)-Lys(Boc)-Tyr(Bzl)-CTC resin is carried out by using 1% TFA in DCM and the resulting solution was neutralized by using 10% DIPEA in DCM. The fractions which were found to be UV positive were collected, combined and evaporated. The crude was dissolved in ethyl acetate and the organic layer was washed with water and sodium chloride solution. The organic layer was dried over sodium sulphate and evaporated to a solid HPhe-Pro(4-OH)Phg-D-Trp(Boc)-Lys(Boc)-Tyr(Bzl)-OH.

Step 8: Cyclization of H-Phe-Pro (4-OP)-Phg-D-Trp (Boc)-Lys(Boc)-Tyr(Bzl)-OH

Linear peptide obtained in step 7 is weighed and transferred to a clean dry flask and dissolved in DMF. Charged 7.5 g of HATU, 3.4 g of HOAT in DMF are dissolved and cooled to 0-5° C., then added 7 ml of N,N-diisopropyl ethyl amine. The mixture is stirred for 4-6 hrs, followed evaporation of DMF solvent. The obtained product was purified by using reverse phase HPLC to obtain cyclo(Phe-Pro (4-OH)-Phg-D-Trp(Boc)-Lys(Boc)-Tyr(Bzl)) of compound 8. (BOC is used as the amine protecting group)

Step 9: Coupling of Cyclo (Phe-Pro(4-OP)-Phg-D-Trp (Boc)-Lys(Boc)-Tyr(Bzl)) Compound 8 with Protected Ethylene Diamine Cyclo (Phe-Pro(4-OH)-Phg-D-Trp(Boc)-Lys(Boc)-Tyr(Bzl)) is added drop wise into a solution of triphosgene in THF to give chlorocarbonate intermediate. After 1 h dimethylaminopyridine and N-Boc diaminoethane are added and the reaction is stirred at room temperature. After completion of the reaction, the solvent is removed under vacuum and the resulting Cyclo (Phe-Pro(4-OCO—NH—CH2-CH2-NH-Boc)-Phg-D-Trp(Boc)-Lys(Boc)-Tyr(Bzl)) with amine protecting groups is treated with TFA/TIS and water (9:5, 2:5, 2:5) for about 2 hrs and isolated by using methyl tertiary butyl ester to give crude Pasireotide.

Step 10: Purification of Crude Pasireotide

The obtained crude Pasireotide in step 9 is purified by preparative HPLC, Pasireotide salt is obtained by using 0.1-1% desired acid as a buffer in a binary gradient method using mixture of water and acetonitrile as a mobile phase. Combine all the fractions collected in the RP purification and lyophilize to get pure Pasireotide or its salt form.

Example-2: Alternative Process for the Preparation of Pasireotide

Step-1:
Synthesis of Fmoc-Phe-CTC Resin 2-chloro trityl resin (CTC-resin) 110 gm (1.2 mmol) was transferred to a peptide reaction vessel and swelled for 1 hr with dichloromethane (DCM). Then the dichloromethane solvent was drained off and washed with dimethyl formamide. To the above resin 14 gm of Fmoc-Phe-OH dissolved in dichloromethane and N, N-diisopropylethyl amine (7.5 ml) was added at 0-5° C. The obtained mixture was stirred for 2 hr and Methanol (10 ml) was added and stirred for another 15 min, then the solvent was drained. The obtained crude was washed with dimethyl formamide and dichloromethane.

Step-2:
Synthesis of Fmoc-Tyr(Bzl)-Phe-CTC Resin

The Fmoc group of Fmoc-Phe-CTC resin was deblocked by treatment with 20% piperidine in dimethyl formamide (DMF) solution for about 20 minutes and washed with dimethyl formamide and Dichloromethane three times alternatively. 12 gm of Fmoc-Tyr(Bzl)-OH and 4.0 gm of HOBt are dissolved in dimethyl formamide in a separate RB flask and cooled to 0-5° C., to this, N'-Diisopropylcarbodiimide (DIDC) (8 ml) was added. The reaction mixture was stirred for about 5 min and added to the above deprotected resin. Then stirred the reaction mixture for 2 hr and washed with DMF, IPA, DCM and DMF to obtain Fmoc-Tyr(Bzl)-Phe-CTC resin.

Step-3:
Synthesis of Fmoc-Lys(Boc)-Tyr(Bzl)-Phe-CTC Resin

The Fmoc group was deprotected by adding 20% piperidine in DMF solution to Fmoc-tyr(Bzl)-Phe-CTC resin for about 20 min and then washed the resin with DMF and DCM alternatively 3 times. 8 gm of Fmoc-Lys(Boc)-OH and 2.8 gm of HOBt were dissolved in DMF and cooled to 0-5° C. Then N,N-diisopropyl carbodiimide (1 ml) was added and activated for about 5 min. The above reaction mixture was added to Tyr(Boc)-Phe-CTC resin and stirred for 2-3 hr then filtered and washed with DMF, IPA, DCM and DMF to obtain Fmoc-Lys(Boc)-Tyr(Bzl)-Phe-CTC resin.

Step-4
Coupling of Fmoc-D-Trp(Boc)-OH to Fmoc-Lys(Boc)-Tyr(Bzl)-Phe-CTC Resin

The Fmoc group was deprotected by adding 20% piperidine in DMF solution to Fmoc-Lys(Boc)-Tyr(Bzl)-Phe-CTC resin for about 20 min and washed the resin with DMF and MDC alternatively 3 times to obtain H-Pro-Phe-D-Trp (Boc)-Lys(Boc)-Tyr(Bzl)-Phe-OH. In a separate RB flask 7.2 gm of Fmoc-D-Trp(Boc)-OH and 2.7 gm of HOBt were dissolved in DMF and cooled to 0-5° C. To this N,N-diisopropyl carbodiimide was added and activated for 5 minutes. The reaction mixture was added to the above deprotected resin and stirred for 2-3 hrs. Then the reaction mixture was filtered and washed the product with DMF, IPA, DCM and DMF to obtain Fmoc-D-Trp(Boc)-Lys(Boc)-Tyr(Bzl)-Phe-CTC resin.

Step-5:
Coupling of Fmoc-Phg-OH to Fmoc-D-Trp(Boc)-Lys (Boc)-Tyr(Bzl)Phe-CTC Resin The Fmoc group was deprotected by adding 20% piperidine in DMF solution to Fmoc-Trp(Boc)-Lys(Boc)-Tyr (Bzl)-phe-Resin for about 20 minutes and washed with DMF and DCM alternatively 3 times. In a separate RB flask 4.5 gm of Fmoc-Phg-OH and 2.2 gm of HOBt were dissolved in DMF and cooled to 0-5° C. Then 4.8 ml of DIC was added and activated for about 5 min. The obtained mixture was added to the above deprotected resin and stirred for 2-2.5 hr at 5-10° C. Filtered the reaction mass and washed with DMF, IPA, DCM and DMF to obtain Fmoc-phg-D-Trp(Boc)-Lys(Boc)-Tyr(Bzl)-Phe-CTC resin.

Step-6:
Coupling of Fmoc-pro-OH to Fmoc-Phg-D-Trp(Boc)-Lys(Boc)-Tyr(Bzl)-Phe-CTC Resin.

The Fmoc group was deprotected by adding 20% piperidine in DMF solution to Phg-D-Trp(Boc)-Lys(Boc)-Tyr(Bzl)-Phe-CTC for about 20 minutes. Filtered and washed the resin with DMF and DCM alternatively 3 times. In a separate RB flask 4 gm of Fmoc-Pro-OH and 2.2 gm of HOBt were dissolved in DMF and cool to 0-5° C. Then 5.2 ml of DIC was added to the above mixture and activated for about 5 minutes. The activated mixture was added to the above deprotected rein and stirred for 2-3 hrs. Filtered and washed the reaction mass with DMF, IPA, DCM and DMF to obtain Fmoc-Pro-Phg-D-Trp(Boc)-Lys(Boc)-Tyr(Bzl)-Phe-CTC Resin.

Step-7:
Cleavage of Resin from Fmoc-Pro-Phg-D-Trp(Boc)-Lys(Boc)-Tyr(Bzl)-Phe-CTC Resin Fmoc group is deprotected by adding 20% piperidine in DMF solution to Fmoc-Pro-Phg-D-Trp(Boc)-Lys(Boc)-Tyr(Bzl)-Phe-CTC Resin for about 20 min and washed with DMF and DCM alternatively 3 times followed by methanol. The obtained compound is completely dried under vacuum for about 2-3 hrs. Finally treated with 1% TFA in DCM followed by neutralization with 10% DIPEA in DCM to obtain resin de protected Pro-Phg-D-Trp(Boc)-Lys(Boc)-Tyr(Bzl)-Phe.

Step-8:
Cyclization of H-Pro-Phe-Phg-D-Trp(Boc)-Lys(Boc)-Tyr(Bzl)-Phe-OH

Linear peptide obtained in step-7 was dissolved in dichloromethane. To this TBTU and 7 ml of N,N-diisopropylethylamine were added. The reaction mixture was stirred for 2 hr at 0-5° C., then raised the temperature to 25° C. and maintained the reaction mass for 2 hr. dichloromethane was distilled off and ethyl acetate was added to the crude. Washed the ethyl acetate layer with water, sodium bicarbonate solution and sodium chloride solution. Distilled of the solvent to obtain cyclo[Pro(4-OH)-Phg-D-Trp(BocO-lys(Boc)-Tyr(Bzl)-Phe] (Mass: 1161)

Step-9:
Coupling of cyclo[Pro(4-OH)-Phg-D-Trp(Boc-lys(Boc)-Tyr(Bzl)-Phe] Compound 8 with Boc Protected Ethylene Diamine 10 gm of cyclo[Pro(4-OH)-Phg-D-Trp(Boc-lys(Boc)-Tyr(Bzl)-Phe] was dissolved in dry dichloromethane and cooled to 0-5° C. To this 1.1 carbonyl diimidazole (5.6 gm) and 4-(dimethyl amino) pyridine (2.2 gm) were added and allowed the reaction mass to room temperature and stirred until completion of reaction. The above reaction mixture was cooled to 0-5° C. and slowly added 8.0 gm Boc Ethylene diamine drop wise at temperature 20-25° C. Maintained the reaction mass for 12 hr and washed with water, saturated sodium bicarbonate solution and saturated sodium chloride solution. The reaction mass was distilled off under vacuum to get cyclo(Pro(4-OCo—NH—CH2-CH2-NH-Boc)-Phg-D-Trp(BoC)-Lys(Boc)-Tyr(Bzl)-Phe] (Mass: 1347).

Step-10:
Deprotection of BOC Group:
cyclo(Pro(4-OCO—NH—CH2-CH2-NH-Boc)-Phg-D-Trp(BoC)-Lys(Boc)-Tyr(Bzl)-Phe] is treated with TFA/Tis/water (9.5:2.5:2.5) for 1 hr at 5-10° C. and Isolated final compound by using methyl tertiary butyl ether to give crude Pasireotide (Mass-1047). The obtained crude is further purified by prep HPLC to obtain Pasireotide with 99.9% purity.

Example-3: Process for the Preparation of Pasireotide Side Chain Fmoc-(2S,4R)-(4-O—CO—NH—CH2-CH2-NH-Boc)-Pro-OH Step-I:
Preparation of Methyl Ester of Fmoc-Hydroxy Proline A clean & dry RBF was charged with 10 gm of Fmoc hydroxyl proline dissolved in Methanol and stirred for 10 min and cooled to 0-5° C. 2.6 ml of thionyl chloride was added drop wise and maintained the total mass for 12 hr at 20-25° C. Evaporate total methanol at 40-45° C. Crude is dissolved in ethyl acetate and washed with water and saturated sodium bicarbonate solution. Distilled off the solvent completely to obtain Fmoc-hydroxy proline methyl ester 10 gm.

Step-II:
Preparation of Fmoc-(2S, 4R)-4(-OCO—NH—CH2-CH2-NH-Boc-Pro-OMe 10 gm of Fmoc-(2S, 4R)-4-hydroxy proline methyl ester was dissolved in dry dichloromethane and stirred for 10 minutes then to cooled to 0-5° C. Charged DMAP (2.8 gm) and CDI (5.5 gm) to the reaction mixture and stirred for 1-2 hr at 5-10° C. Boc protected ethylene diamine was added slowly to the above reaction mass and raised the temperature to 20-25° C. Stirred the reaction mass for 2-4 and washed the reaction mass with water. Distilled off the solvent completely and isolated with methyl tertiary butyl ether.

Yield: 70%

Step-III:
Preparation of Fmoc-(2S,4R)-(4-O—CO—NH—CH2-CH2-NH-Boc)-Pro-OH

The methyl ester obtained in step-II was then hydrolyzed to free acid by treatment with 1N sodium hydroxide in a mixture of 1, 4-dioxane and water. Providing a mixture of H-(2S,4R)-(4OCO—NH—$CH_2$—$CH_2$—NH-Boc)-Pro-OH and the desired product Fmoc-(2S,4R)-(4OCO—NH—$CH_2$—$CH_2$—NH-Boc)-Pro-OH.

Yield: 55%

The above described process steps for the synthesis of Pasireotide is further represented in below shown process flow chart. The process starts from coupling of Chlorotrityl Chloride-resin (CTC-resin) with Fmoc-Tyr(Bzl)-OH to give Fmoc-Tyr(Bzl)-CTC which on further multiple steps comprising deblockings of Fmoc, couplings, cleavage and cyclization results Cyclo (Phe-Pro(4-OP)-Phg-D-Trp(Boc)-Lys(Boc)-Tyr(Bzl) of formula 8. Coupling of compound of formula 8 with N-Boc diaminoethane in presence of phosgene gives Pasireotide. Optionally thus obtained Pasireotide is further purified by preparative HPLC.

We claim:
1. A process for preparing Pasireotide of formula (11) comprising the steps of:
(a) treating 2-chloro Trityl Resin (CTC resin) with Fmoc-Tyr(Bzl)-OH in presence of DCM and N,N-diisopropylethylamine (DIPEA) to obtain Fmoc-Tyr(Bzl)-CTC resin;

(b) coupling Fmoc-Lys(Boc)-OH with Fmoc-Tyr(Bzl)-CTC resin in presence of HOBt and HBTU, DMF, and N,N-diisopropyl ethyl amine (DIPEA) to obtain Fmoc-Lys(Boc)-Tyr(Bzl)-CTC resin;
(c) coupling of Fmoc-D-Trp(Boc)-OH with Fmoc-Lys(Boc)-Tyr(Bzl)-CTC resin in presence of HOBt and TBTU in DMF and N,N-diisopropyl ethylamine to obtain Fmoc-D-Trp(Boc)-Lys(Boc)-Tyr(Bzl)-CTC resin;
(d) coupling Fmoc-Phg-OH with Fmoc-D-Trp(Boc)-Lys(Boc)-Tyr(Bzl)-CTC resin in presence of HOAT and DIC in DMF and N-Methyl morpholine (NMM) to obtain Fmoc-Phg-D-Trp(Boc)-Lys(Boc)-Tyr(Bzl)-CTC resin;
(e) coupling Fmoc-Pro(4-OP)-OH with Fmoc-Phg-D-Trp(Boc)-Lys(Boc)-Tyr(Bzl)-CTC-resin in presence of HOBt and DIC in DMF and N-Methyl morpholine (NMM) to obtain Fmoc-Pro (4-OP)-Phg-D-Trp(Boc)-Lys(Boc)-Tyr(Bzl)-CTC resin, wherein P is a hydrogen or a hydroxyl protecting group;
(f) coupling Fmoc-Phe-OH with Pro(4-OP)-Phg-D-Trp(Boc)-Lys(Boc)-Tyr(Bzl)-CTC resin in presence of HBTU and HOBt in DMF and N,N-diisopropyl ethylamine (DIPEA) to obtain Fmoc-Phe-Pro(4-OP)-Phg-D-Trp(Boc)-Lys(Boc)-Tyr(Bzl)-CTC resin wherein P is a hydrogen or a hydroxyl protecting group;
(g) cleaving the resin from Fmoc-Phe-Pro(4-OP)-Phg-D-Trp(Boc)-Lys(Boc)-Tyr(Bzl)-CTC resin using TFA in DCM followed by neutralizing using DIPEA in DCM to obtain a solid H-Phe-Pro(4-OP)Phg-D-Trp(Boc)-Lys(Boc)-Tyr(Bzl)-OH wherein P is a hydrogen or a hydroxyl protecting group;
(h) cyclizing of H-Phe-Pro-(4-OP)-Phg-D-Trp(Boc)-Lys(Boc)-Tyr(Bzl)-OH in presence of HATU and HOAT in DMF and N,N-diisopropyl ethyl amine (DIPEA) to obtain cyclo(Phe-Pro(4-OP)-Phg-D-Trp(Boc)-Lys(Boc)-Tyr(Bzl)) (compound 8) wherein P is a hydrogen or a hydroxyl protecting group;
(i) coupling of cyclo(Phe-Pro(4-OP)-Phg-D-Trp(Boc)-Lys(Boc)-Tyr(Bzl)) (compound 8) with N-Boc diaminoethane in presence of triphosgene in THF to give a chlorocarbonate intermediate wherein P is a hydrogen or a hydroxyl protecting group;
(j) deprotecting the amine protecting groups in the chlorocarbonate intermediate by treating with TFA/TIS and water to give crude Pasireotide;
(k) optionally, purifying crude Pasireotide by preparative HPLC and further converting into Pasireotide salt by treating with desired acid.

2. A process for the preparing Pasireotide of formula (11) comprising the steps of:
(a) treating 2-chloro trityl resin (CTC resin) with Fmoc-Phe-OH in dichloromethane and N,N-diisopropylethyl amine to obtain Fmoc-Phe-CTC resin;
(b) coupling Fmoc-Phe-CTC resin with Fmoc-Tyr(Bzl)-OH in presence of HOBt in dimethyl formamide and N,N'-Diisopropylcarbodiimide (DIDC) to obtain Fmoc-Tyr(Bzl)-Phe-CTC resin;
(c) coupling Fmoc-Tyr(Bzl)-Phe-CTC resin with Fmoc-Lys(Boc)-OH in presence of HOBt in DMF and N,N'-diisopropyl carbodiimide to obtain Fmoc-Lys(Boc)-Tyr(Bzl)-Phe-CTC resin;
(d) coupling Fmoc-D-Trp(Boc)-OH with Fmoc-Lys(Boc)-Tyr(Bzl)-Phe-CTC resin in presence of HOBt in DMF and N,N'-diisopropyl carbodiimide to obtain Fmoc-D-Trp(Boc)-Lys(Boc)-Tyr(Bzl)-Phe-CTC resin;
(e) coupling Fmoc-Phg-OH with Fmoc-D-Trp(Boc)-Lys(Boc)-Try(Bzl)Phe-CTC Resin in presence of HOBt and DIC in DMF to obtain Fmoc-Phg-D-Trp(Boc)-Lys(Boc)-Tyr(Bzl)-Phe-CTC resin;
(f) coupling Fmoc-Pro-OH with Fmoc-Phg-D-Trp(Boc)-Lys(Boc)-Tyr(Bzl)-Phe-CTC resin in presence of HOBt and DIC in DMF to obtain Fmoc-Pro-Phg-D-Trp(Boc)-Lys(Boc)-Tyr(Bzl)-Phe-CTC resin;
(g) cleaving the resin from Fmoc-Pro-Phg-D-Trp(Boc)-Lys(Boc)-Tyr(Bzl)-Phe-CTC resin by treating with TFA in DCM followed by neutralizing with DIPEA in DCM to obtain resin deprotected Pro-Phg-D-Trp(Boc)-Lys(Boc)-Tyr(Bzl)-Phe;
(h) cyclizing of H-Pro-Phe-Phg-D-Trp(Boc)-Lys(Boc)-Tyr(Bzl)-Phe-OH in presence of dichloromethane, TBTU and N,N-diisopropylethylamine to obtain cyclo[Pro(4-OH)-Phg-D-Trp(Boc)-Lys(Boc)-Tyr(Bzl)-Phe] (compound 8);
(i) coupling of cyclo[Pro(4-OH)-Phg-D-Trp(Boc)-Lys(Boc)-Tyr(Bzl)-Phe] compound 8 with Boc protected Ethylene diamine in dichloromethane solvent using carbonyl diimidazole and 4-(dimethyl amino) pyridine to provide cyclo(Pro(4-OCO—NH—CH$_2$—CH$_2$—NH-Boc)-Phg-D-Trp(Boc)-Lys(Boc)-Tyr(Bzl)-Phe];
(j) deprotecting the Boc groups of cyclo(Pro(4-OCO—NH—CH$_2$—CH$_2$—NH-Boc)-Phg-D-Trp(Boc)-Lys(Boc)-Tyr(Bzl)-Phe] by treating with TFA/TIS/water to give crude Pasireotide;
(k) optionally purifying crude Pasireotide as obtained above by preparative HPLC to obtain Pasireotide with 99.9% purity.

* * * * *